United States Patent
Leatherman et al.

(10) Patent No.: US 8,263,669 B2
(45) Date of Patent: Sep. 11, 2012

(54) HYDROLYSIS RESISTANT ORGANOMODIFIED TRISILOXANE IONIC SURFACTANTS

(75) Inventors: Mark D. Leatherman, Stamford, CT (US); George A. Policello, Ossining, NY (US); Wenging N. Peng, Shanghai (CN); Liping Zheng, Shanghai (CN); Roland Wagner, Bonn (DE); Suresh K. Rajaraman, Macungie, PA (US); Xia Zijun, Shanghai (CN)

(73) Assignee: Momentive Performance Materials Inc., Albany, NY (US)

( * ) Notice: Subject to any disclaimer, the term of this patent is extended or adjusted under 35 U.S.C. 154(b) by 68 days.

(21) Appl. No.: 12/810,976

(22) PCT Filed: Dec. 26, 2008

(86) PCT No.: PCT/US2008/014068
§ 371 (c)(1),
(2), (4) Date: Oct. 4, 2010

(87) PCT Pub. No.: WO2009/085300
PCT Pub. Date: Jul. 9, 2009

(65) Prior Publication Data
US 2011/0021644 A1    Jan. 27, 2011

Related U.S. Application Data

(63) Continuation of application No. 11/964,186, filed on Dec. 26, 2007, now abandoned.

(51) Int. Cl.
*B01F 3/08* (2006.01)
*C07F 7/10* (2006.01)
(52) U.S. Cl. ............. 516/55; 516/20; 516/53; 516/67; 516/68; 556/413; 556/424
(58) Field of Classification Search ................. None
See application file for complete search history.

(56) References Cited

U.S. PATENT DOCUMENTS

| | | |
|---|---|---|
| 2007/0197394 A1 | 8/2007 | Policello et al. |
| 2008/0090963 A1 | 4/2008 | Rajaraman et al. |

FOREIGN PATENT DOCUMENTS

| | | |
|---|---|---|
| EP | 0353687 | 2/1990 |
| EP | 0535596 | 4/1993 |
| JP | 07-062102 | 3/1995 |
| JP | 08-257390 | 10/1996 |
| WO | 00/50491 | 8/2000 |
| WO | 2008/111926 | 9/2008 |
| WO | 2008/111928 | 9/2008 |

OTHER PUBLICATIONS

"Synthesis of Ionic Surfactants based on Epoxy-functionalized (Poly)siloxanes" authored by Maciejewski et al. and published in Przemsyl Chemiczny (2006) 85 (8-9, Pt. 1), 946-949.*
"Trisiloxane Surfactants—Mechanisms of Spreading and Wetting" published in Pesticide Formulations and Application Systems: 18th volume, ASTM STP 1347.*
"Zwitterionic Organofunctional Siloxanes as Aqueous Surfactants: Synthesis and Characterization of Betaine Functional Siloxanes and their Comparison to Sulfobetaine-Functional Siloxanes" authored by Snow et al., and published in Langmuir (1991) 7, 868-871.*

* cited by examiner

*Primary Examiner* — Marc Zimmer
(74) *Attorney, Agent, or Firm* — Dominick G. Vicari

(57) ABSTRACT

The present invention provides for a composition comprising a siloxane having the formula: $M^1 D\ M^2$ wherein $M^1=(R^1)(R^2)(R^3)SiO_{1/2}$; $M^2=(R^4)(R^5)(R^6)SiO_{1/2}$ and $D=(R^7)(Z)SiO_{2/2}$ where $R^1, R^2, R^3, R^4, R^5, R^6$ and $R^7$ are each independently selected from the group consisting of 1 to 4 carbon monovalent hydrocarbon radicals, aryl, and a hydrocarbon group of 4 to 9 carbons containing an aryl group; Z is a pendant hydrophilic ionic group selected from the group consisting of $R^8$—$R^A$, $R^9\ R^c$ and $R^{10}$—$R^Z$; $R^A$ being an anionic substituent, $R^c$ a cationic substituent or $R^z$ a zwitterionic substituent on the D group wherein the composition is resistant to hydrolysis under either basic or acidic conditions.

10 Claims, No Drawings

HYDROLYSIS RESISTANT ORGANOMODIFIED TRISILOXANE IONIC SURFACTANTS

This application is a 371 national stage of PCT/US2008/014068 filed Dec. 26, 2008 which is a continuation of U.S. application Ser. No. 11/964,186 filed Dec. 26, 2007, now abandoned.

FIELD OF THE INVENTION

The present invention relates to trisiloxane surfactant compositions that exhibit resistance to hydrolysis over a wide pH range. More particularly the present invention relates to such hydrolysis resistant trisiloxane surfactants having a resistance to hydrolysis between a pH of about 3 to a pH of about 12.

BACKGROUND OF THE INVENTION

The topical application of liquid compositions to the surfaces of both animate and inanimate objects to effect a desired change involve the processes of controlling wetting, spreading, foaming, detergency, and the like. When used in aqueous solutions to improve the delivery of active ingredients to the surface being treated, trisiloxane type compounds have been found to be useful in enabling the control of these processes to achieve the desired effect. However, the trisiloxane compounds may only be used in a narrow pH range, ranging from a slightly acidic pH of 6 to a very mildly basic pH of 7.5. Outside this narrow pH range, the trisiloxane compounds are not stable to hydrolysis undergoing a rapid decomposition.

SUMMARY OF THE INVENTION

The present invention provides for a composition comprising a siloxane having the formula:

$$M^1 D M^2$$

wherein $$M^1 = (R^1)(R^2)(R^3)SiO_{1/2};$$

$$M^2 = (R^4)(R^5)(R^6)SiO_{1/2} \text{ and}$$

$$D = (R^7)(Z)SiO_{2/2}$$

where $R^1$, $R^2$, $R^3$, $R^4$, $R^5$, $R^6$ and $R^7$ are each independently selected from the group consisting of 1 to 4 carbon monovalent hydrocarbon radicals, aryl, and a hydrocarbon group of 4 to 9 carbons containing an aryl group;

Z is a hydrophilic substituent selected from the group consisting of $R^8$—$R^A$, $R^9$—$R^C$, and $R^{10}$—$R^Z$;

$R^8$ is a divalent radical selected from the group consisting of $R^{11}(O)_t(R^{12})_u(O)_v$,

selected from the group consisting

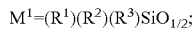

and
$R^{14}O(C_2H_4O)_a(C_3H_6O)_b(C_4H_8O)_c$;

where $R^{11}$ and $R^{12}$ are each independently selected from the group consisting of a divalent hydrocarbon group of 1 to 4 carbon atoms, that may each be optionally substituted with one or more OH radicals;

$R^{13}$ is a divalent hydrocarbon group of 2 to 4 carbon atoms;

$R^{14}$ is a divalent hydrocarbon group of 1 to 6 carbons, that may each be optionally branched; subscripts t, u and v are zero or 1; t the subscripts a, b and c are zero or positive and satisfy the following relationships:

$$1 \leq a+b+c \leq 10 \text{ with } a \geq 1;$$

$R^A$ is a monovalent radical selected from the group consisting of $SO_3M^K$, —C(=O)CH$_2$CH(R$^{15}$)COOM$^K$; —PO$_3$HM$^K$; COOM$^K$; where $R^{15}$ is H or SOM$^K$;

$M^K$ is a cation selected from the group consisting of Na$^+$, K$^+$, Ca$^{2+}$, NH$_4^+$, Li$^+$, and monovalent ammonium ions derived from mono-, di- and trialkylamines of 2 to 4 carbons or mono-, di- and trialkanolamines of 2 to 4 carbons;

$R^9$ is a monovalent radical selected from the group consisting of $R^{16}(O)_w(R^{17})_x$ and $R^{18}O(C_2H_4O)_d(C_3H_6O)_e(C_4H_8O)_fCH_2CH(OH)CH_2$;

where $R^{16}$ and $R^{17}$ are each independently selected from the group consisting of a divalent hydrocarbon group of 1 to 4 carbon atoms, that may each be optionally substituted with one or more OH radicals;

$R^{18}$ is a divalent hydrocarbon group of 2 to 4 carbon atoms; subscripts w and x are zero or 1;

the subscripts d, e and f are zero or positive and satisfy the following relationships:

$$1 \leq d+e+f \leq 10 \text{ with } d \geq 1;$$

$R^C$ is selected from the group consisting of $N(R^{19})(R^{20})$,

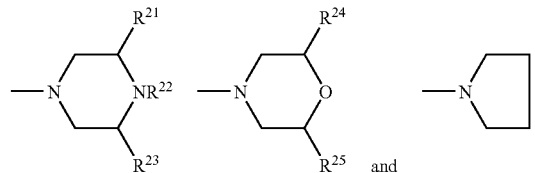

where $R^{19}$ and $R^{20}$ are independently selected from the group consisting of H, a branched or linear monovalent hydrocarbon radical of 1 to 4 carbons;

$R^{26}N(R^{29})(R^{30})$, and —$R^{27}O(C_2H_4O)_g(C_3H_6O)_h(C_4H_8O)_iR^{28}$;

the subscripts g, h and i are zero or positive and satisfy the following relationships:

$$1 \leq g+h+i \leq 10 \text{ with } g \geq 1.$$

$R^{21}$, $R^{23}$, $R^{24}$, $R^{25}$ are independently selected from the groups consisting of H, a branched or linear monovalent hydrocarbon radical of 1 to 4 carbons;

$R^{22}$ is H, a branched or linear monovalent hydrocarbon radical of 1 to 4 carbons, or —$R^{31}O(C_2H_4O)_j(C_3H_6O)_k(C_4H_8O)_lR^{32}$;

the subscripts j, k and l are zero or positive and satisfy the following relationships:

$$1 \leq j+k+l \leq 10 \text{ with } j \geq 1;$$

$R^{26}$ is a divalent hydrocarbon radical of 1 to 6 carbons that may be optionally substituted with a heterocyclic group containing nitrogen, sulfur, oxygen or combinations thereof or $R^{33}O(C_2H_4O)_m(C_3H_6O)_n(C_4H_8O)_oR^{34}$;

the subscripts m, n and o are zero or positive and satisfy the following relationships:

$$1 \leq m+n+o \leq 10 \text{ with } m \geq 1;$$

$R^{29}$ and $R^{30}$ are independently selected from the group consisting of H or a branched or linear monovalent hydrocarbon radical of 1 to 4 carbons;

$R^{27}$, $R^{31}$ and $R^{33}$ are divalent radicals independently selected from the group consisting of a divalent hydrocarbon group of 2 to 4 carbon atoms;

$R^{28}$ is H, a monovalent hydrocarbon radical of 1 to 6 carbons, or $N(R^{35})(R^{36})$;

$R^{32}$ and $R^{34}$ are independently selected from the group consisting of H, a branched or linear monovalent hydrocarbon radical of 1 to 4 carbons, and $R^{37}N(R^{38})(R^{39})$; where $R^{37}$ is a divalent hydrocarbon radical of 1 to 6 carbons;

$R^{35}$, $R^{36}$, $R^{38}$ and $R^{39}$ are independently selected from the group consisting of H and branched or linear monovalent hydrocarbon radicals of 1 to 4 carbons;

$R^{10}$ is a monovalent radical selected from the group consisting of $R^{40}(O)_y(R^{41})_z$ and $R^{42}O(C_2H_4O)_p(C_3H_6O)_q(C_4H_8O)_rCH_2CH(OH)CH_2$;

where $R^{40}$ and $R^{41}$ are each independently selected from the group consisting of a divalent hydrocarbon bridging group of 1 to 4 carbon atoms, that may be each optionally substituted with one or more OH radicals;

$R^{42}$ is a divalent hydrocarbon group of 2 to 4 carbon atoms; subscripts y and z are zero or 1;

the subscripts p, q and r are zero or positive and satisfy the following relationships:

$$1 \leq p+q+r \leq 10 \text{ with } p \geq 1.$$

$R^Z$ is a monovalent radical selected from the group consisting of
$N-(R^{43})(R^{44})_\alpha R^{45}SO_3^-(M^K)_\beta$, $N-(R^{46})(R^{47})_\gamma R^{48}COO^-(M^K)_\delta$,
$N^+-(R^{49})(R^{50})R^{51}OP(=O)(A)(B)$ or,
$(-C(=O)N(R^{52})R^{53}N-(R^{54})(R^{55}))^+-(R^{56}OP(=O)(A)(B))(X)_\epsilon$;

where $R^{43}$, $R^{44}$, $R^{46}$, $R^{47}$, $R^{49}$, $R^{50}$, $R^{52}$, $R^{54}$ and $R^{55}$ are independently selected from the group consisting of H, a branched or linear monovalent hydrocarbon radical of 1 to 4 carbons, and an alkanolamine group of 2 to 4 carbons;

$R^{45}$ is a divalent group of 3 to 4 carbons;

The subscripts $\alpha$, $\beta$, $\gamma$ and $\delta$ are zero or 1 subject to the following relationships: $\alpha+\beta=1$ and $\gamma+\delta=1$;

$R^{48}$ and $R^{51}$ are independently a divalent group of 1 to 4 carbons;

$R^{53}$ and $R^{56}$ are each independently a divalent group of 2 to 4 carbons;

A and B are selected from the group consisting of $O^-$ and $OM^K$;

X is an anion selected from the group of anions consisting of Cl, Br, and I;

and the subscript $\epsilon$ is 0, 1 or 2. The present invention further provides for various emulsions of the composition of the present invention.

DETAILED DESCRIPTION OF THE INVENTION

As used herein, integer values of stoichiometric subscripts refer to molecular species and non-integer values of stoichiometric subscripts refer to a mixture of molecular species on a molecular eight average basis, a number average basis or a mole fraction basis.

As used herein the term emulsion is an inclusive term describing mixtures comprising two or more phases wherein at least one phase is discontinuous, regardless of how finely divided that phase may be. The term includes, but is not limited to simple emulsions, emulsions within emulsions, micro-emulsions, macro-emulsions and the like.

The present invention provides for a trisiloxane compound or compositions thereof useful as a surfactant having the formula:

$$M^1 D M^2$$

wherein $$M^1=(R^1)(R^2)(R^3)SiO_{1/2}$$

$$M^2=(R^4)(R^5)(R^6)SiO_{1/2}$$

$$D=(R^7)(Z)SiO_{2/2}$$

where $R^1$, $R^2$, $R^3$, $R^4$, $R^5$, $R^6$ and $R^7$ are each independently selected from the group consisting of 1 to 4 carbon monovalent hydrocarbon radicals, aryl, and a hydrocarbon group of 4 to 9 carbons containing an aryl group; Z is a hydrophilic substituent selected from the group consisting of $R^8-R^A$, $R^9-R^C$, and $R^{10}-R^Z$; $R^8$ is a monovalent radical selected from the group consisting of $R^{11}(O)_t(R^{12})_u(O)_v$, $R^{13}-CHCH_2CH(OH)CH(O-)CH_2CH_2$; and $R^{14}O(C_2H_4O)_a(C_3H_6O)_b(C_4H_8O)_c$;

where $R^{11}$ and $R^{12}$ are each independently selected from the group consisting of a divalent hydrocarbon group of 1 to 4 carbon atoms, that may each be optionally substituted with one or more OH radicals; $R^{13}$ is a divalent hydrocarbon group of 2 to 4 carbon atoms; $R^{14}$ is a divalent hydrocarbon group of 1 to 6 carbons, that may each be optionally branched; subscripts t, u and v are zero or 1. The subscripts a, b and c are zero or positive and satisfy the following relationships:

$$1 \leq a+b+c \leq 10 \text{ with } a \geq 1.$$

$R^A$ is a monovalent radical selected from the group consisting of $SO_3M^K$, $-C(=O)CH_2CH(R^{15})COOM^K$; $-PO_3HM^K$; $COOM^K$; where $R^{15}$ is H or $SOM^K$;

and $M^K$ is a cation selected from the group consisting of $Na^+$, $K^+$, $Ca^{2+}$, $NH_4^+$, $Li^+$, and monovalent ammonium ions derived from mono-, di- and trialkylamines of 2 to 4 carbons or mono-, di- and trialkanolamines of 2 to 4 carbons.

$R^9$ is a monovalent radical selected from the group consisting of $R^{16}(O)_w(R^{17})_x$, $R^{18}O(C_2H_4O)_d(C_3H_6O)_e(C_4H_8O)_fCH_2CH(OH)CH_2$;

where $R^{16}$ and $R^{17}$ are each independently selected from the group consisting of a divalent hydrocarbon group of 1 to 4 carbon atoms, that may each be optionally substituted with one or more OH radicals; $R^{18}$ is a divalent hydrocarbon group of 2 to 4 carbon atoms; subscripts w and x are zero or 1. The subscripts d, e and f are zero or positive and satisfy the following relationships:

$$1 \leq d+e+f \leq 10 \text{ with } d \geq 1.$$

$R^C$ is selected from the group consisting of $N(R^{19})(R^{20})$,

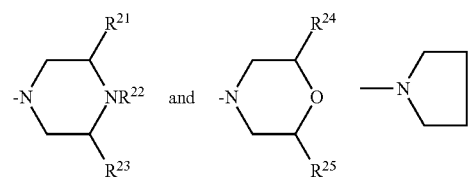

where $R^{19}$ and $R^{20}$ are independently selected from the group consisting of H, a branched or linear monovalent hydrocarbon radical of 1 to 4 carbons, $R^{26}N(R^{29})(R^{30})$, and —$R^{27}O(C_2H_4O)_g(C_3H_6O)_h(C_4H_8O)_iR^{28}$. The subscripts g, h and i are zero or positive and satisfy the following relationships:

$$1 \leq g+h+i \leq 10 \text{ with } g \geq 1.$$

$R^{21}$, $R^{23}$, $R^{24}$, $R^{25}$ are independently selected from the groups consisting of H, a branched or linear monovalent hydrocarbon radical of 1 to 4 carbons.

$R^{22}$ is H, a branched or linear monovalent hydrocarbon radical of 1 to 4 carbons, or —$R^{31}O(C_2H_4O)_j(C_3H_6O)_k(C_4H_8O)_lR^{32}$; the subscripts j, k and l are zero or positive and satisfy the following relationships:

$$1 \leq j+k+l \leq 10 \text{ with } j \geq 1.$$

$R^{26}$ is a divalent hydrocarbon radical of 1 to 6 carbons, optionally substituted with a heterocyclic group containing nitrogen, sulfur, oxygen or combinations thereof or $R^{33}O(C_2H_4O)_m(C_3H_6O)_n(C_4H_3O)_oR^{34}$; the subscripts m, n and o are zero or positive and satisfy the following relationships:

$$1 \leq m+n+o \leq 10 \text{ with } m \geq 1.$$

$R^{29}$ and $R^{30}$ are independently selected from the group consisting of H or a branched or linear monovalent hydrocarbon radical of 1 to 4 carbons.

$R^{27}$, $R^{31}$ and $R^{33}$ are divalent radicals independently selected from the group consisting of a divalent hydrocarbon group of 2 to 4 carbon atoms.

$R^{28}$ is H, a monovalent hydrocarbon radical of 1 to 6 carbons, or $N(R^{35})(R^{36})$.

$R^{32}$ and $R^{34}$ are independently selected from the group consisting of H, a branched or linear monovalent hydrocarbon radical of 1 to 4 carbons, and $R^{37}N(R^{38})(R^{39})$; where $R^{37}$ is a divalent hydrocarbon radical of 1 to 6 carbons. $R^{35}$, $R^{36}$, $R^{38}$ and $R^{39}$ are independently selected from the group consisting of H and branched or linear monovalent hydrocarbon radicals of 1 to 4 carbons.

$R^{10}$ is a monovalent radical selected from the group consisting of $R^{40}(O)_y(R^{41})_z$, or $R^{42}O(C_2H_4O)_p(C_3H_6O)_q(C_4H_8O)_rCH_2CH(OH)CH_2$;

where $R^{40}$ and $R^{41}$ are each independently selected from the group consisting of a divalent hydrocarbon bridging group of 1 to 4 carbon atoms, each optionally OH substituted; $R^{42}$ is a divalent hydrocarbon group of 2 to 4 carbon atoms; subscripts y and z are zero or 1. The subscripts p, q and r are zero or positive and satisfy the following relationships:

$$1 \leq p+q+r \leq 10 \text{ with } p \geq 1.$$

$R^Z$ is a monovalent radical selected from the group consisting of N—$(R^{43})(R^{44})_\alpha R^{45}SO_3^-(M^K)_\beta$, N—$(R^{46})(R^{47})_\gamma$ $R^{48}COO^-(M^K)_\delta$, $N^+$-$(R^{49})(R^{50})R^{51}OP(=O)(A)(B)$ or, $(—C(=O)N(R^{52})R^{53}N—(R^{54})(R^{55}))^+—(R^{56}OP(=O)(A)(B))(X)_\epsilon$;

from the group consisting of H, a branched or linear monovalent hydrocarbon radical of 1 to 4 carbons, and an alkanolamine group of 2 to 4 carbons. $R^{45}$ is a divalent bridging group of 3 to 4 carbons; subscripts $\alpha$, $\beta$, $\gamma$, $\delta$ and $\epsilon$ are zero or 1 subject to the following relationships: $\alpha+\beta=1$ and $\gamma+\delta=1$.

$R^{48}$ and $R^{51}$ are independently a divalent group of 1 to 4 carbons.

$R^{53}$ and $R^{56}$ are each independently a divalent group of 2 to 4 carbons. $M^K$ is a cation selected from the group consisting of $Na^+$, $K^+$, $Ca^{2+}$, $NH_4^+$, $Li^+$, and monovalent ammonium ions derived from mono-, di- and trialkylamines of 2 to 4 carbons or mono-, di- and trialkanolamines of 2 to 4 carbons. A and B are selected from the group consisting of $O^-$ and $OM^K$; X is an anion selected from the group of anions consisting of Cl, Br, and I; the subscript $\epsilon$ is 0, 1 or 2.

Particularly useful embodiments of the present invention are exemplified by the following choices for species:

$R^1$ and $R^4$ are propyl, isopropyl, butyl, sec-butyl, iso-butyl, or tert-butyl; $R^2$, $R^3$, $R^5$, $R^6$, $R^7$ is methyl; $R^{11}$ is —$CH_2CH_2CH_2$—; $R^{12}$ is —$CH_2CH(OH)CH_2$—; $R^{13}$ is —$H_2CH_2$—; $R^{14}$ is —$CH_2CH_2CH_2$—, —$CH(CH_3)CH_2CH_2$—, or —$CH_2CH(CH_3)CH_2$—; a, b and c=0; t=1, u=1, v=0; $R^{15}$=H; $M^K$ is $Na^+$, $K^+$ or $NH_4^+$; $R^{16}$ is —$H_2CH_2CH_2$—; $R^{17}$ is $CH_2CH(OH)CH_2$—; $R^{18}$ is —$CH_2CH_2CH_2$—; d, e, and f=0; w=1, x=1; $R^{19}$ and $R^{20}$ is H, methyl, ethyl, propyl, isopropyl or —$R^{27}O(C_2H_4O)_g(C_3H_6O)_h(C_4H_8O)_iR^{28}$; $R^{27}$ is —$CH_2CH_2CH_2$—; g is 1-5, h and i=0; $R^{27}$ is H or methyl; $R^{21}$ and $R^{23}$ are H; $R^{22}$=H, methyl or —$^{31}O(C_2H_4O)_j(C_3H_6O)_k(C_4H_8O)_lR^{32}$; $R^{31}$ is —$CH_2CH_2CH_2$—; j is 1-5, k and l=0; $R^{32}$ is H or methyl; $R^{24}$ and $R^{25}$ are H; $R^{40}$ is —$CH_2CH_2CH_2$—; $R^{41}$ is —$H_2CH(CH_3)CH_2$—;

y and z=1; $R^{42}$ is —$CH_2CH_2CH_2$—; p is 1-5, q and r=0; $R^{43}$ and $R^{44}$ are H or methyl; $R^{45}$ is —$CH_2CH_2CH_2$— or —$CH_2CH_2CH_2CH_2$—; $M^K$=$Na^+$, $K^+$ or $NH_4^+$;

$R^{46}$ and $R^{47}$ are H or methyl; $R^{48}$ is —$CH_2CH_2CH_2$— or —$CH_2CH_2CH_2CH_2$—;

$R^{49}$ and $R^{50}$ are H or methyl; and $R^{52}$, $R^{54}$ and $R^{55}$ are H or methyl.

Additionally, the compositions described above are also useful as the alkyl chloride, alkyl iodide and alkyl bromide analogues, as well as the acid pairs with HCl, acetic acid, propionic acid, glycolic acid, gibberellic acid and the like. One skilled in the art understands the benefits of quaternization, which increases solubility and as well as makes possible potential interactions with nonionic and anionic co-surfactants.

Epoxy-modified organofunctional trisiloxanes are straightforwardly prepared through the use of a hydrosilylation reaction to graft the olefinically modified (i.e. vinyl, allyl or methallyl) epoxy group onto the hydride (SiH) intermediate of the organomodified trisiloxane of the present invention.

Precious metal catalysts suitable for making epoxy-substituted siloxanes are also well known in the art and comprise complexes of rhodium, ruthenium, palladium, osmium, iridium, and/or platinum. Many types of platinum catalysts for this SiH-olefin addition reaction are known and such platinum catalysts may be used to generate the compositions of the present invention. The platinum compound can be selected from those having the formula ($PtCl_2$Olefin) and H($PtCl_3$Olefin) as described in U.S. Pat. No. 3,159,601, hereby incorporated by reference. A further platinum-containing material can be a complex of chloroplatinic acid with up to 2 moles per gram of platinum of a member selected from the class consisting of alcohols, ethers, aldehydes and mixtures thereof as described in U.S. Pat. No. 3,220,972 hereby incorporated by reference. Yet another group of platinum containing materials useful in this present invention is described in U.S. Pat. Nos. 3,715,334; 3,775,452 and 3,814,730 (Karstedt). Additional background concerning the art may be found in J. L. Spier, "Homogeneous Catalysis of Hydrosilation by Transition Metals", in Advances in Organometallic Chemistry, volume 17, pages 407 through 447, F. G. A. Stone and R. West editors, published by Academic Press (New York, 1979). Those skilled in the art can easily determine an effective amount of platinum catalyst. Generally an effective amount ranges from about 0.1 to 50 parts per million of the total organomodified trisiloxane composition.

The compositions of the present invention exhibit an enhanced resistance to hydrolysis outside a pH range ranging from 6 to 7.5. Enhanced resistance to hydrolysis can be demonstrated by a variety of tests but as used herein enhanced resistance to hydrolysis means 50 mole percent or more of the hydrolysis-resistant composition of the present invention remains unchanged or unreacted after a period of a twenty-four exposure to aqueous acidic conditions where the solution has a pH lower than 6 or after a period of a twenty-four hour exposure to aqueous basic conditions where the solution has a pH greater than 7.5. Under acidic conditions the compositions of the present invention show a survival of 50 mole percent of the original concentration or greater at a pH of 5 or less for a period of time in excess of 48 hours; specifically the compositions of the present invention show a survival of 50 mole percent or greater at a pH of 5 or less for a period of time in excess of 2 weeks; more specifically the compositions of the present invention show a survival of 50 mole percent or greater at a pH of 5 or less for a period of time in excess of 1 month; and most specifically the compositions of the present invention show a survival of 50 mole percent or greater at a pH of 5 or less for a period of time in excess of 6 months. Under basic conditions the compositions of the present invention show a survival of 50 mole percent or greater at a pH of 8 or more for a period of time in excess of 2 weeks; specifically the compositions of the present invention show a survival of 50 mole percent or greater at a pH of 8 or more for a period of time in excess of 4 weeks; more specifically the compositions of the present invention show a survival of 50 mole percent or greater at a pH of 8 or more for a period of time in excess of 6 months; and most specifically the compositions of the present invention show a survival of 50 mole percent or greater at a pH of 8 or more for a period of time in excess of 1 year.

Uses for the Compositions of the Present Invention:

The compositions of the present are useful as surfactants in a variety of applications. The compositions of the present invention may be utilized as pure components, mixtures, or emulsions. As is generally known, emulsions comprise at least two immiscible phases one of which is continuous and the other which is discontinuous. Further emulsions may be liquids or gases with varying viscosities or solids. Additionally the particle size of the emulsions may render them microemulsions and when sufficiently small microemulsions may be transparent. Further it is also possible to prepare emulsions of emulsions and these are generally known as multiple emulsions. These emulsions may be:

1) aqueous emulsions where the discontinuous phase comprises water and the continuous phase comprises the composition of the present invention;

2) aqueous emulsions where the discontinuous phase comprises the composition of the present invention and the continuous phase comprises water;

3) non-aqueous emulsions where the discontinuous phase comprises a non-aqueous hydroxylic solvent and the continuous phase comprises the composition of the present invention; and 4) non-aqueous emulsions where the continuous phase comprises a non-aqueous hydroxylic organic solvent and the discontinuous phase comprises the composition of the present invention.

A. Pesticide—Agriculture, Horticulture, Turf, Ornamental and Forestry:

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, enhance spreading to improve spray coverage, or to provide penetration of the herbicide into the plant cuticle. These adjuvants are provided either as a tank-side additive or used as a component in pesticide formulations.

Typical uses for pesticides include agricultural, horticultural, turf, ornamental, home and garden, veterinary and forestry applications.

The pesticidal compositions of the present invention also include at least one pesticide, where the composition of the present invention is present at an amount sufficient to deliver between 0.005% and 2% to the final use concentration, either as a concentrate or diluted in a tank mix. Optionally the pesticidal composition may include excipients, co-surfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides that can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, flu oxystrobin, dimoxystrobin, azoxystrobin, furcaranil, prochloraz, flusulfamide, famoxadone, captan, maneb, mancozeb, dodicin, dodine, and metalaxyl.

Insecticide, larvacide, miticide and ovacide compounds that can be used with the composition of the present invention, but not limited to, *Bacillus thuringiensis*, spinosad, abamectin, doramectin, lepimectin, pyrethrins, carbaryl, primicarb, aldicarb, methomyl, amitraz, boric acid, chlordimeform, novaluron, bistrifluoron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

The pesticide may be a liquid or a solid. If a solid, it is preferable that it is soluble in a solvent, or the organomodified trisiloxanes of the present invention, prior to application, and the silicone may act as a solvent, or surfactant for such solubility or additional surfactants may perform this function.

B. Agricultural Excipients:

Buffers, preservatives and other standard excipients known in the art also may be included in the composition.

Solvents may also be included in compositions of the present invention. These solvents are in a liquid state at room temperature. Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents would be 2,2,4-trimethyl, 1-3-pentane diol and alkoxylated (especially ethoxylated) versions thereof as illustrated in U.S. Pat. No. 5,674,832 herein incorporated by reference, or n-methyl-pyrrilidone.

C. Co-Surfactants:

Moreover, other co-surfactants, which have short chain hydrophobes that do not interfere with superspreading as described in U.S. Pat. Nos. 5,558,806, 5,104,647, and 6,221,811, herein included by reference.

The co-surfactants useful herein include nonionic, cationic, anionic, amphoteric, zwitterionic, polymeric surfactants, or any mixture thereof. Surfactants are typically hydrocarbon based, silicone based or fluorocarbon based.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates. and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

Specific examples include alkyl acetylenic diols (SURFO-NYL-Air Products), pyrrlodone based surfactants (e.g., SURFADONE—LP 100-ISP), 2-ethyl hexyl sulfate, isodecyl alcohol ethoxylates (e.g., RHODASURF DA 530—Rhodia), ethylene diamine alkoxylates (TETRONICS—BASF), and ethylene oxide/propylene oxide copolymers (PLURONICS—BASF) and Gemini type surfactants (Rhodia).

Preferred surfactants include ethylene oxide/propylene oxide copolymers (EO/PO); amine ethoxylates; alkyl polyglycosides; oxo-tridecyl alcohol ethoxylates; and so forth.

In a preferred embodiment, the agrochemical composition of the present invention further comprises one or more agrochemical ingredients. Suitable agrochemical ingredients include, but not limited to, herbicides, insecticides, growth regulators, fungicides, miticides, acaricides, fertilizers, biologicals, plant nutritionals, micronutrients, biocides, paraffinic mineral oil, methylated seed oils (i.e. methylsoyate or methylcanolate), vegetable oils (such as soybean oil and canola oil), water conditioning agents such as Choice® (Loveland Industries, Greeley, Colo.) and Quest (Helena Chemical, Collierville, Tenn.), modified clays such as Surround® (Englehard Corp.), foam control agents, surfactants, wetting agents, dispersants, emulsifiers, deposition aids, anti-drift components, and water.

Suitable agrochemical compositions are made by combining, in a manner known in the art, such as, by mixing one or more of the above components with the organomodified trisiloxane of the present invention, either as a tank-mix, or as an "In-can" formulation. The term "tank-mix" means the addition of at least one agrochemical to a spray medium, such as water or oil, at the point of use. The term "In-can" refers to a formulation or concentrate containing at least one agrochemical component. The "In-can" formulation may then diluted to use concentration at the point of use, typically in a Tank-mix, or it may be used undiluted.

D. Coatings:

Typically coatings formulations will require a wetting agent or surfactant for the purpose of emulsification, compatibilization of components, leveling, flow and reduction of surface defects. Additionally, these additives may provide improvements in the cured or dry film, such as improved abrasion resistance, antiblocking, hydrophilic, and hydrophobic properties. Coatings formulations may exists as solvent-borne coatings, water-borne coatings and powder coatings.

The coatings components may be employed as architecture coatings, OEM product coatings such as automotive coatings and coil coatings, and special purpose coatings such as industrial maintenance coatings and marine coatings.

Typical resin types include polyesters, alkyds, acrylics, and epoxies.

E. Personal Care

In a preferred embodiment, the composition of the present invention comprises, per 100 parts by weight ("pbw") of the personal care composition, from 0.1 to 99 pbw, more preferably from 0.5 pbw to 30 pbw and still more preferably from 1 to 15 pbw of the composition and from 1 pbw to 99.9 pbw, more preferably from 70 pbw to 99.5 pbw, and still more preferably from 85 pbw to 99 pbw of the personal care composition.

The compositions of the present invention may be utilized in personal care emulsions, such as lotions, and creams. As is generally known, emulsions comprise at least two immiscible phases one of which is continuous and the other which is discontinuous. Further emulsions may be liquids with varying viscosities or solids. Additionally the particle size of the emulsions may render them microemulsions and when sufficiently small microemulsions may be transparent. Further it is also possible to prepare emulsions of emulsions and these are generally known as multiple emulsions. These emulsions may be:

1) aqueous emulsions where the discontinuous phase comprises water and the continuous phase comprises the composition of the present invention;

2) aqueous emulsions where the discontinuous phase comprises the composition of the present invention and the continuous phase comprises water;

3) non-aqueous emulsions where the discontinuous phase comprises a non-aqueous hydroxylic solvent and the continuous phase comprises the composition of the present invention; and 4) non-aqueous emulsions where the continuous phase comprises a non-aqueous hydroxylic organic solvent and the discontinuous phase comprises the composition of the present invention.

Non-aqueous emulsions comprising a silicone phase are described in U.S. Pat. Nos. 6,060,546 and 6,271,295 the disclosures of which are herewith and hereby specifically incorporated by reference.

As used herein the term "non-aqueous hydroxylic organic compound" means hydroxyl-containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a cream or lotion with improved deposition properties and good feel characteristics. It is capable of being blended into formulations for hair care, skin care, antiperspirants, sunscreens, cosmetics, color cosmetics, insect repellants, vitamin and hormone carriers, fragrance carriers and the like.

The personal care applications where the composition of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a preferred embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the composition. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In one useful embodiment, an antiperspirant composition comprises the composition of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the composition, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylm ethane, p-aminobenzoic acid and octyl dimethyl-p-aminobenzoic acid.

In another useful embodiment, a color cosmetic composition, such as, for example, a lipstick, a makeup or a mascara composition comprises the composition, and a coloring agent, such as a pigment, a water soluble dye or a liposoluble dye.

In another useful embodiment, the compositions of the present invention are utilized in conjunction with fragrant materials. These fragrant materials may be fragrant compounds, encapsulated fragrant compounds, or fragrance releasing compounds that either the neat compounds or are encapsulated. Particularly compatible with the compositions of the present invention are the fragrance releasing silicon containing compounds as disclosed in U.S. Pat. Nos. 6,046,156, 6,054,547, 6,075,111, 6,077,923, 6,083,901, and 6,153,578, all of which are herein and herewith specifically incorporated by reference.

The uses of the compositions of the present invention are not restricted to personal care compositions; other products such as waxes, polishes and textiles treated with the compositions of the present invention are also contemplated.

F. Home Care

Home care applications include laundry detergent and fabric softener, dishwashing liquids, wood and furniture polish, floor polish, tub and tile cleaners, toilet bowl cleaners, hard surface cleaners, window cleaners, antifog agents, drain cleaners, auto-dish washing detergents and sheeting agents, carpet cleaners, prewash spotters, rust cleaners and scale removers.

G. Oil and Gas

Compositions of the present organomodified silylated surfactant invention are useful in oil and gas applications, including demulsification.

H. Water Processing

Compositions comprising organomodified silylated surfactant invention are useful for applications involving commercial and industrial open recirculating cooling water towers, closed cooling water systems, cooling water conduits, heat exchangers, condensers, once-through cooling systems, Pasteurizers, air washers, heat exchange systems, air conditioning/humidifiers/dehumidifiers, hydrostatic cookers, safety and/or fire water protection storage systems, water scrubbers, disposal wells, influent water systems, including filtration and clarifiers, wastewater treatment, wastewater treatment tanks, conduits, filtration beds, digesters, clarifiers, holding ponds, settling lagoons, canals, odor control, ion exchange resin beds, membrane filtration, reverse osmosis, micro- and ultra-filtration, assisting in the removal of biofilms in cooling tower applications, heat exchangers and process water systems, and the like.

I. Pulp and Paper

Compositions of the present organomodified silylated surfactant invention are useful in pulp and paper applications, such as paperboard defoamers, and wetting agents for the pulping process.

EXPERIMENTAL

The hydride intermediates for the compositions of the present invention, as well as comparative compositions were prepared as described in the following examples.

Preparation Example 1

1,5-Di(tert-butyl)-1,1,3,5,5, Pentamethyltrisiloxane (FIG. 1). (tert-butyl)Dimethylchlorosilane (100 g) and methyldichlorosilane (46 g) were dissolved in 150 mL isopropylether (IPE) and placed in an addition funnel. 150 g water and 250 mL IPE were charged to a 1 L round bottom flask equipped with a mechanical stirrer, reflux condenser and $N_2$ inlet. The chlorosilanes were added dropwise via the addition funnel at room temperature (23° C.) over a period of 1 hour. After addition was complete, the temperature was adjusted to 70° C., maintained for 20 h and progress followed by GC (88% yield at 20 h). When the reaction was complete, the water was drained off via a separation funnel. The organic layer was washed 3 times using 100 g of water each time. 25 g of NaHCO$_3$ was mixed with 100 g of water, added slowly to the mixture and stirred for 30 min. The aqueous layer was separated and drained, and the organic layer was dried over sodium sulfate. After filtering, the IPE was stripped off on the rotor evaporator and the crude product was further fractional distilled under reduced pressure to afford 63 g tBuMe$_2$SiOMe(H)SiOSiMe$_2$tBu (GC purity 97%).

Figure 1. Reaction Sequence for Preparation of Hydride Intermediate 1.

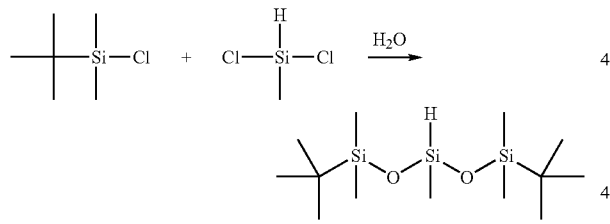

Preparation Example 2

1,5-Di(iso-propyl)-1,1,3,5,5, Pentamethyltrisiloxane (FIG. 2) (iso-propyl)Dimethylchlorosilane (25 g) and methyldichlorosilane (13.1 g) were dissolved in 80 mL isopropylether (IPE) and placed in an addition funnel. Water (50 g) and IPE (100 mL) were charged to a 500 mL round bottom flask equipped with a mechanical stirrer, reflux condenser and $N_2$ inlet. The chlorosilanes were added dropwise via the addition funnel at room temperature (23° C.) over a period of 40 minutes. After the addition was complete, the temperature was adjusted to 80° C. and maintained for 4 h. Reaction progress was followed by GC (75% yield at 4 h). When the reaction was complete, the aqueous layer was drained off via a separation funnel. The organic layer was washed 3 times using 80 g of water each time. 25 g of NaHCO$_3$ was mixed with 100 g of water and added slowly to the organic layer and stirred for 30 min. The aqueous layer was again drained and dried over sodium sulfate. After filtration, the IPE was stripped off on the rotary evaporator and the crude product was further fractional distilled under reduced pressure to afford 10 g of the desired product (GC purity 93%).

Figure 2. Reaction Sequence for Preparation of Hydride Intermediate 2.

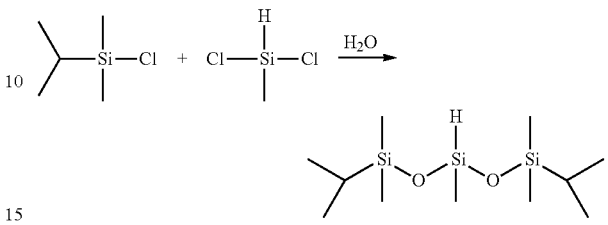

Preparation Example 3

1,5-Di(tert-butyl)-3-(oxiranylmethylpropyl)-1,1,3,5,5-Pentamethyltrisiloxane (FIG. 3). 1,5-Di(tert-butyl)-1,1,3,5,5,-Pentamethyltrisiloxane (24.5 g) and Karstedt's catalyst (30 ppm) were charged to a 100 mL RB 3 neck flask equipped with a magnetic stirrer, reflux condenser and $N_2$ inlet. The mixture was stirred and heated to 90° C. 2-Allyloxymethyloxirane (10.0 g) was placed in an addition funnel and added dropwise to the mixture in the flask. The mixture was stirred and maintained at 90° C. for an additional 4 hours. The reaction progress was followed by NMR spectroscopy. Upon completion of the reaction, the excess 2-allyloxymethyl-oxirane was removed by vacuum distillation.

Figure 3. Reaction Sequence for Preparation of Epoxide Intermediate 3.

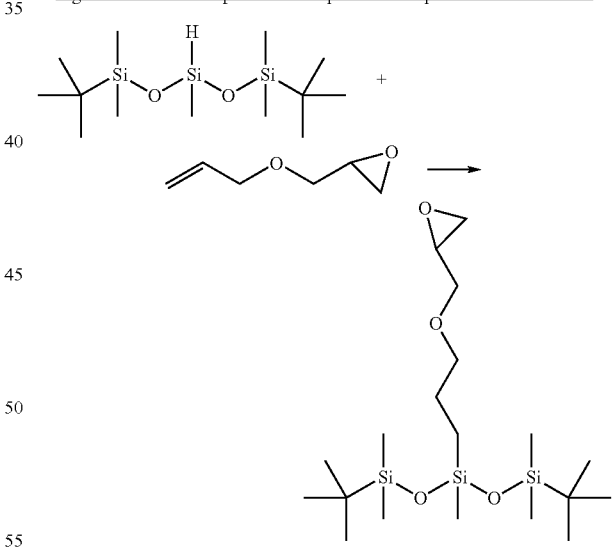

Preparation Example 4

1-(3-(Di(tert-butyldimethylsiloxy)-methyl-silanyl)-propoxy)-3-(4-(2-hydroxy-ethyl)-piperidin-1-yl)-propan-2-ol (FIG. 4). 2-piperazin-1-yl-ethanol (0.61 g) and ethanol (20 mL) were charged to a 100 mL RB flask equipped with a magnetic stirrer. The mixture was stirred and heated to 70° C. 1,5-Di(tert-butyl)-3-(oxiranylmethylpropyl)-1,1,3,5,5-Pentamethyltrisiloxane (2.0 g) was placed in an addition funnel and added dropwise to the flask. The mixture was stirred and maintained at 70° C. for an additional 4 hours. The reaction progress was monitored by NMR spectroscopy. Upon reaction completion, the ethanol was removed by rotovap, and the mixture was distilled under reduced pressure to remove impurities.

Figure 4. Reaction Sequence for Preparation of Trisiloxane Surfactant 4.

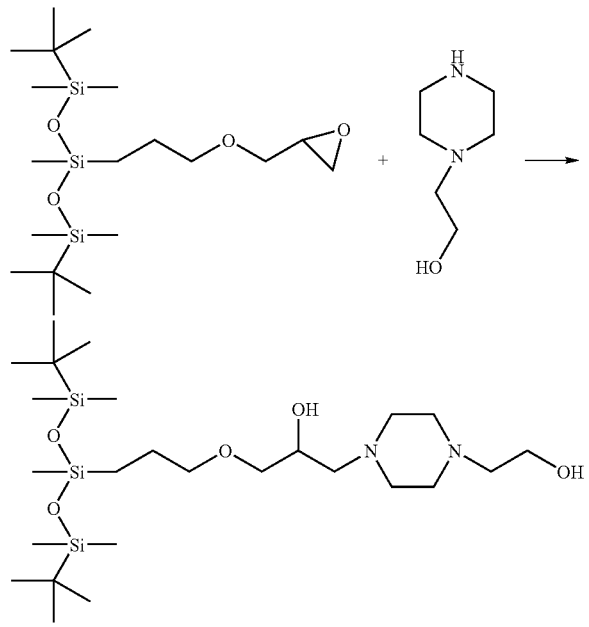

Preparation Example 5

1-(3-(Di(tert-butyldimethylsiloxy)-methyl-silanyl)-propoxy)-3-(2-(2-hydroxy-ethoxy)-ethylamino)-propan-2-ol (FIG. 5). 2-(2-Amino-ethoxy)-ethanol (2.50 g) and ethanol (40 mL) were charged to a 100 mL RB flask equipped with a magnetic stirrer. The mixture was stirred and heated to 70° C. 1,5-Di(tert-butyl)-3-(oxiranylmethylpropyl)-1,1,3,5,5-Pentamethyltrisiloxane (2.0 g) mixed with ethanol (10 mL) was placed in an addition funnel and added dropwise to the flask. The mixture was stirred and maintained at 70° C. for an additional 4 hours. Reaction progress was monitored by NMR spectroscopy. Upon reaction completion, the ethanol was removed by rotary evaporation, and the mixture was distilled under vacuum to remove impurities and excess raw material.

Figure 5. Reaction Sequence for Preparation of Trisiloxane Surfactant 5.

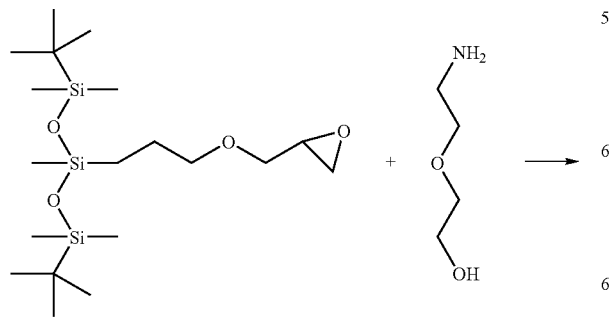

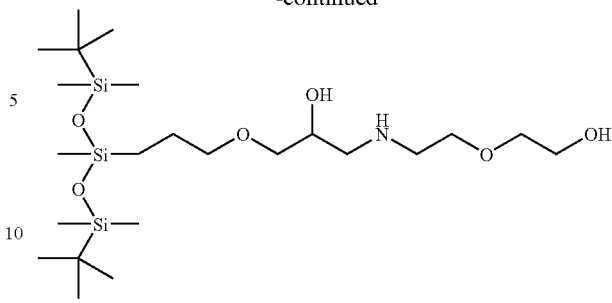

Preparation Example 6

1-(3-(Di(tert-butyldimethylsiloxy)-methyl-silanyl)-propoxy)-3-(2-(2-(2-hydroxy-ethoxy)-ethoxy)-ethylamino)-propan-2-ol (FIG. 6). 2-(2-(2-Amino-ethoxy)-ethoxy)-ethanol (3.52 g) and ethanol (40 mL) were charged to a 100 mL RB flask equipped with a magnetic stirrer. The mixture was stirred and heated to 70° C. 1,5-Di(tert-butyl)-3-(oxiranylmethylpropyl)-1,1,3,5,5-Pentamethyltrisiloxane (2.0 g) mixed with ethanol (10 mL) was placed in an addition funnel and added dropwise to the flask. The mixture was stirred and maintained at 70° C. for an additional 4 hours. Reaction progress was monitored by NMR spectroscopy. Upon reaction completion, the ethanol was removed by rotary evaporation, and the mixture was distilled under vacuum to remove impurities and excess raw material.

Figure 6. Reaction Sequence for Preparation of Trisiloxane Surfactant 6.

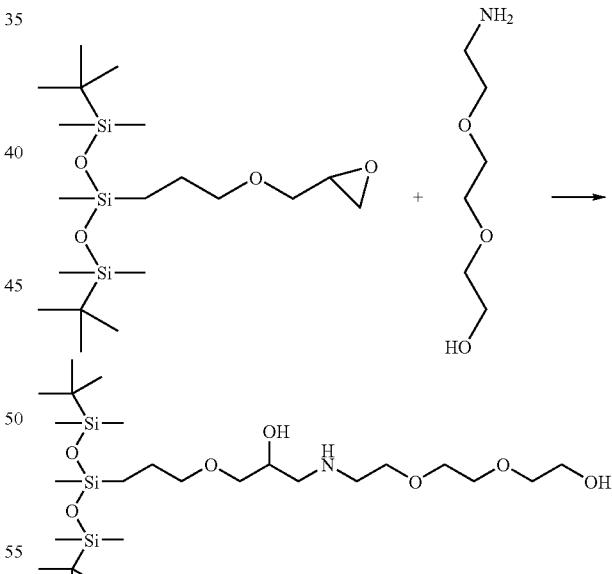

Preparation Example 7

1,5-Di(tert-butyl)-3-(N,N-dimethylaminopropyl)-1,1,3,5,5-Pentamethyltrisiloxane (FIG. 7). 1,5-Di(tert-butyl)-1,1,3,5,5-Pentamethyltrisiloxane and Karstedt's catalyst (30 ppm) were charged to a 100 mL Schlenk flask. The mixture was heated to 90° C. and N,N-dimethyl allyl amine (4.48 g) was added dropwise via syringe over 5 minutes. After complete addition, the reaction temperature was maintained at 90° C. for 3 hrs and the reaction was monitored by ¹HNMR spectroscopy. Upon reaction completion, the volatiles were removed at 100° C./0.1 mmHg, and 15.2 g light yellow oil product was obtained.

Figure 7. Reaction Sequence for Preparation of Trisiloxane Amine Intermediate 7.

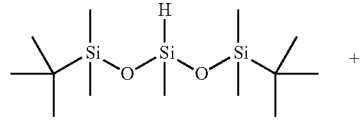
+
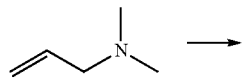
→
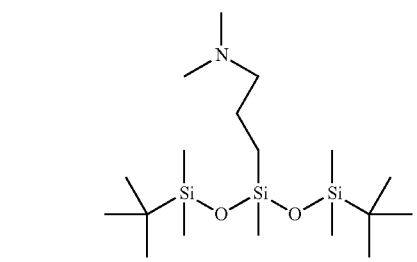

Preparation Example 8

3-((3-(Di(tert-butyldimethylsiloxy)-methyl-silanyl)-propyl)-dimethyl-amino)-propane-1-sulfonate (FIG. 8). 1,5-Di(tert-butyl)-3-(N,N-dimethylaminopropyl)-1,1,3,5,5-Pentamethyltrisiloxane (3.91 g) and 1,3-propanesultone (1.28 g) were dissolved in dry THF (10 mL), and charged to a round bottom flask equipped with magnetic stirrer, reflux condenser and N₂ inlet. The mixture was heated to reflux overnight. After removal of solvent under reduced pressure, the residue was washed with hexane and filtered. 4.82 g white solid product was obtained.

Figure 8. Reaction Sequence for Preparation of Trisiloxane Surfactant 8.

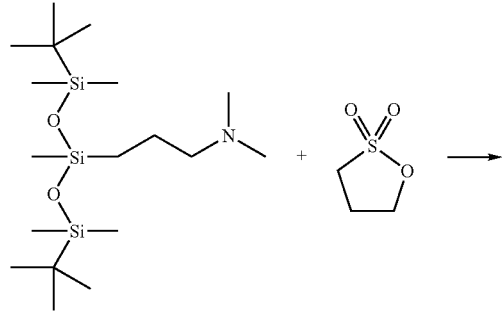

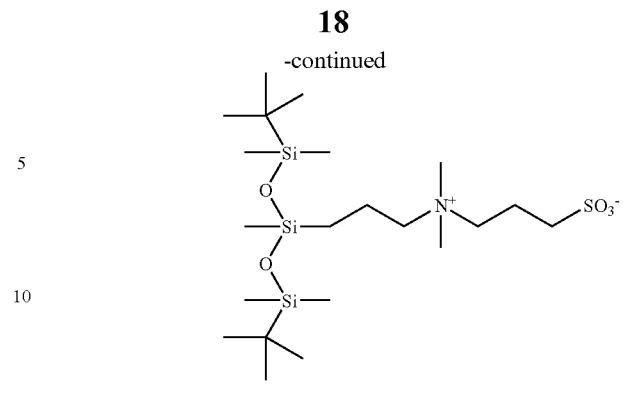

Preparation Example 9

3-((3-(Di(tert-butyldimethylsiloxy)-methyl-silanyl)-propyl)-dimethyl-amino)-butane-1-sulfonate (FIG. 9). N,N-dimethyl aminopropyl-di-t-butyl pentamethyl trisiloxane (1.96 g) and 1,4-butanesultone (0.72 g) were dissolved in dry acetone (10 mL) and charged to a round bottom flask equipped with magnetic stirrer, reflux condenser and N₂ inlet. The mixture was heated to reflux overnight. After removal of solvent under reduced pressure, the residue was washed with hexane and filtered. 2.46 g white solid product was obtained.

Figure 9. Reaction Sequence for Preparation of Trisiloxane Surfactant 9.

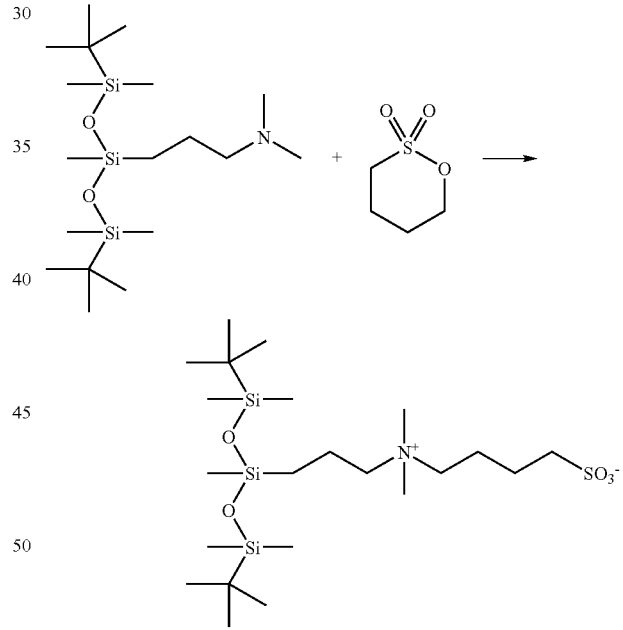

Preparation Example 10

3-((3-(Di(tert-butyldimethylsiloxy)-methyl-silanyl)-propyl)-dimethyl-amino)-acetate (FIG. 10). N,N-dimethyl aminopropyl-di-t-butyl pentamethyl trisiloxane (1.96 g) and sodium 2-bromoacetate (0.81 g) were dissolved in absolute ethanol (20 mL) and charged to a round bottom flask equipped with magnetic stirrer, reflux condenser and N₂ inlet. The suspension was heated to reflux overnight until all sodium 2-bromoacetate disappeared. After removal of solvent under reduced pressure, the residue was washed with hexane and filtered. 2.56 g white solid product was obtained.

Figure 10. Reaction Sequence for Preparation of Trisiloxane Surfactant 10.

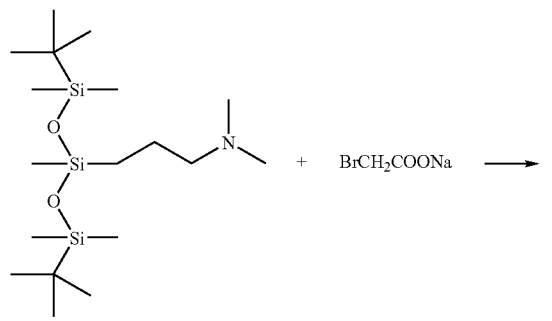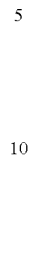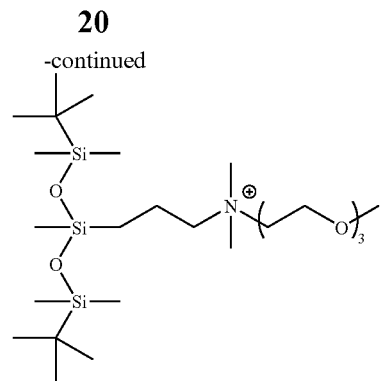

Preparation Example 11

1,5-(Di(tert-butoxy)-3-(3-((2-(2-(2-Methoxy-ethoxy)-ethoxy)-ethyl)-dimethyl-amino)-propyl)-pentamethyltrisiloxane (FIG. 11). N,N-dimethyl aminopropyl-di-t-butyl pentamethyl trisiloxane (1.96 g) and 2-(2-chloroethoxy)ethoxyethanol (1.26 g) were dissolved in absolute ethanol (10 mL) and charged to a round bottom flask equipped with magnetic stirrer, reflux condenser and $N_2$ inlet. The mixture was heated to reflux for 20 hrs. After removal of solvent under reduced pressure, the residue was dried under vacuum at 100° C./0.1 mmHg to remove residual volatiles. 1.38 g yellow oil product was obtained.

Figure 11. Reaction Sequence for Preparation of Trisiloxane Surfactant 11.

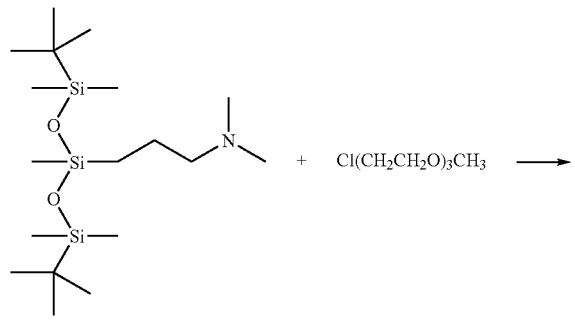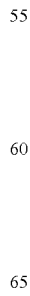

Example 12

This example demonstrates the ability of the organomodified trisiloxane compositions of the present invention to reduce aqueous surface tension thereby showing utility as surfactants. Surface tension was measured using a Kruss surface tensiometer, with a sand blasted platinum blade as the sensor. Solutions of the various components were prepared at 0.1 wt % in 0.005M NaCl water (Deionized), as an equilibrium aid, or at 0.1 wt. % in 2M $NH_4Cl$ solution. Table 1 shows that solutions of these unique compositions provide a significant reduction in surface tension relative to the conventional surfactant.

The compositions of the present invention also provide spreading properties similar to the comparative trisiloxane surfactant (Silwet L-77*, Momentive Performance Materials, Inc., Wilton, Conn.). Additionally, compositions of the present invention provide improved spreading relative to a conventional organic surfactant product OPE-10. Comparative sample OPE-10 (Octylphenolethoxylate, containing 10 polyoxyethylene units) is a non-silicone organic surfactant. This product is available as Triton® X-100 from Dow Chemical Company, Midland, Mich.

Spreading was determined by applying a 10 µL droplet of 0.1 wt. % surfactant solution in water, aqueous ammonium chloride, aqueous sodium chloride, or acetic acid, to polyacetate film (USI, "Crystal Clear Write on Film") and measuring the spread diameter (mm) after 30 seconds, at a relative humidity between 50 and 70% (at 22 to 25° C.). The solution was applied with an automatic pipette to provide droplets of reproducible volume. Deionized water that was further purified with a Millipore filtration system was used to prepare the surfactant solutions.

TABLE 1

Surface Tension and Spreading Properties

| I.D. | Surface Tension | | | Spread Diameter (mm) | | | |
|---|---|---|---|---|---|---|---|
| | Water | 2M $NH_4Cl$ | 10% NaCl | Water | 10% NaCl | 2M $NH_4Cl$ | 10% $CH_3COOH$ |
| 4 | nd | 22.3 | nd | nd | nd | 7 | 16 |
| 5 | nd | 23.7 | nd | nd | nd | 6 | 28 |
| 6 | nd | 22.2 | nd | nd | nd | 7 | 6 |
| 8 | 22.9 | nd | 21.6 | nd | 40 | nd | nd |
| 9 | nd | nd | 22.5 | nd | 12 | nd | nd |
| 10 | 22.3 | nd | 22.2 | 10 | 11 | nd | nd |
| 11 | 23.0 | nd | 22.5 | nd | 8 | nd | nd |
| A | 20.6 | nd | nd | 53 | nd | nd | nd |
| OPE | 31.9 | nd | nd | 9 | nd | nd | nd |

Example 13

Unlike traditional siloxane based surfactants, which are subject to rapid hydrolysis under acidic and basic conditions (at pH values of 5 or below and at pH values of 9 or above) the compositions of the present invention provide increased resistance to hydrolysis relative to traditional trisiloxane alkoxylates (Comparative A). An artifact of hydrolysis is observed as a reduction in spreading properties over time. Therefore solutions of the compositions of the present invention, as well as comparative surfactants were prepared at desired use levels and pH. Spreading was determined as a function of time to illustrate resistance to hydrolysis.

Table 2 is an illustrative example of the compositions of the present invention, where product No. 8, a superspreader, has improved resistance to hydrolysis, over a pH range from pH 4 to pH 10, relative to a traditional trisiloxane ethoxylate surfactant (Comparative A, shown in Table 3). As mentioned above, resistance to hydrolysis was observed by monitoring the spreading properties over time. Here a 0.5 wt % solution of the surfactant in Preparation Example 8 was prepared at pH 4, 5 and 10 in 10% aqueous NaCl system, and a 0.5 wt % solution of the surfactant in Comparative Example A was prepared at pH 4, 5 and 10 in buffered aqueous system. Spreading was determined according to the procedure in Example 12.

TABLE 2

Effect of pH on Spreading Properties Vs Time for Surfactant in Preparation Example 8

| Time | Spread Diameter (mm) | | |
|---|---|---|---|
| | pH 4 | pH 5 | pH 10 |
| 0 h | 35 | 38 | 37 |
| 24 h | 36 | 38 | 35 |
| 48 h | 38 | 38 | 30 |
| 8 days | 38 | 40 | 32 |
| 15 days | 38 | 39 | 38 |
| 29 days | 38 | 40 | 36 |
| 60 days | 37 | 40 | 36 |

TABLE 3

Effect of pH on Spreading Properties Vs Time for Comparative Example A

| Time | Spread Diameter (mm) | | |
|---|---|---|---|
| | pH 4 | pH 5 | pH 10 |
| 0 h | 28 | 29 | 27 |
| 8 h | 31 | 29 | 27 |
| 24 h | 32 | 25 | 25 |
| 48 h | 41 | 25 | 33 |
| 5 days | 30 | 26 | 36 |
| 1 wks | 17 | 28 | 25 |
| 2 wks | 7 | 37 | 15 |

The foregoing examples are merely illustrative of the invention, serving to illustrate only some of the features of the present invention. The appended claims are intended to claim the invention as broadly as it has been conceived and the examples herein presented are illustrative of selected embodiments from a manifold of all possible embodiments. Accordingly it is Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of:" Where necessary, ranges have been supplied; those ranges are inclusive of all sub-ranges there between. Such ranges may be viewed as a Markush group or groups consisting of differing pairwise numerical limitations which group or groups is or are fully defined by its lower and upper bounds, increasing in a regular fashion numerically from lower bounds to upper bounds. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims. All United States patents (and patent applications) referenced herein are herewith and hereby specifically incorporated by reference in their entirety as though set forth in full.

The invention claimed is:

1. A composition comprising a siloxane having the formula:

$$M^1 D M^2$$

wherein $M^1 = (R^1)(R^2)(R^3)SiO_{1/2}$;

$M^2 = (R^4)(R^5)(R^6)SiO_{1/2}$ and $D = (R^7)(Z)SiO_{2/2}$ where $R^1$, $R^2$, $R^3$, $R^4$, $R^5$, $R^6$ and $R^7$ are each independently selected from the group consisting of 1 to 4 carbon monovalent hydrocarbon radicals, aryl, and a hydrocarbon group of 4 to 9 carbons containing an aryl group;

Z is a hydrophilic substituent $R^9-R^c$;

$R^9$ is a monovalent radical selected from the group consisting of $R^{16}(O)_w(R^{17})_x$ and $R^{18}O(C_2H_4O)_d(C_3H_6O)_e(C_4H_8O)_fCH_2CH(OH)CH_2$;

where $R^{16}$ and $R^{17}$ are each independently selected from the group consisting of a divalent hydrocarbon group of 1 to 4 carbon atoms, that may each be optionally substituted with one or more OH radicals;

$R^{18}$ is a divalent hydrocarbon group of 2 to 4 carbon atoms;

subscripts w and x are zero or 1;

the subscripts d, e and f are zero or positive and satisfy the following relationships:

$1 \leq d+e+f \leq 10$ with $d \geq 1$;

$R^C$ is selected from the group consisting of $N(R^{19})(R^{20})$,

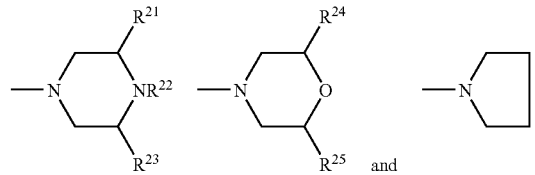

and where $R^{19}$ and $R^{20}$ are independently selected from the group consisting of H, a branched or linear monovalent hydrocarbon radical of 1 to 4 carbons, $R^{26}N(R^{29})(R^{30})$, and $-R^{27}O(C_2H_4O)_g(C_3H_6O)_h(C_4H_8O)_iR^{28}$;

the subscripts g, h and i are zero or positive and satisfy the following relationships:

$$1 \leq g+h+i \leq 10 \text{ with } g \geq 1;$$

$R^{21}$, $R^{23}$, $R^{24}$, $R^{25}$ are independently selected from the groups consisting of H, a branched or linear monovalent hydrocarbon radical of 1 to 4 carbons;

$R^{22}$ is H, a branched or linear monovalent hydrocarbon radical of 1 to 4 carbons, or —$R^{31}O(C_2H_4O)_j(C_3H_6O)_k(C_4H_8O)_lR^{32}$;

the subscripts j, k and l are zero or positive and satisfy the following relationships:

$$1 \leq j+k+l \leq 10 \text{ with } j \geq 1;$$

$R^{26}$ is a divalent hydrocarbon radical of 1 to 6 carbons that may be optionally substituted with a heterocyclic group containing nitrogen, sulfur, oxygen or combinations thereof or $R^{33}O(C_2H_4O)_m(C_3H_6O)_n(C_4H_8O)_oR^{34}$;

the subscripts m, n and o are zero or positive and satisfy the following relationships:

$$1 \leq m+n+o \leq 10 \text{ with } m \geq 1;$$

$R^{29}$ and $R^{30}$ are independently selected from the group consisting of H or a branched or linear monovalent hydrocarbon radical of 1 to 4 carbons;

$R^{27}$, $R^{31}$ and $R^{33}$ are divalent radicals independently selected from the group consisting of a divalent hydrocarbon group of 2 to 4 carbon atoms;

$R^{28}$ is H, a monovalent hydrocarbon radical of 1 to 6 carbons, or $N(R^{35})(R^{36})$;

$R^{32}$ and $R^{34}$ are independently selected from the group consisting of H, a branched or linear monovalent hydrocarbon radical of 1 to 4 carbons, and $R^{37}N(R^{38})(R^{39})$; where $R^{37}$ is a divalent hydrocarbon radical of 1 to 6 carbons; $R^{35}$, $R^{36}$, $R^{38}$ and $R^{39}$ are independently selected from the group consisting of H and branched or linear monovalent hydrocarbon radicals of 1 to 4 carbons.

2. The composition of claim 1 where
$R^1$ and $R^4$ are propyl, isopropyl, butyl, sec-butyl, iso-butyl, or tert-butyl;
$R^2$, $R^3$, $R^5$, $R^6$, $R^7$ is methyl;
$R^{16}$ is —$H_2CH_2CH_2$—;
$R^{17}$ is $CH_2CH(OH)CH_2$—;
$R^{18}$ is —$CH_2CH_2CH_2$—;
$R^{19}$ and $R^{20}$ is H, methyl, ethyl, propyl, isopropyl or—$R^{27}O(C_2H_4O)_g(C_3H_6O)_h(C_4H_8O)_iR^{28}$;
$R^{27}$ is —$CH_2CH_2CH_2$—, H or methyl;
$R^{21}$ and $R^{23}$ are H;
$R^{22}$=H, methyl or —$R^{31}O(C_2H_4O)_j(C_3H_6O)_k(C_4H_8O)_lR^{32}$;
$R^{31}$ is —$CH_2CH_2CH_2$—; j is 1-5, k and l=0;
$R^{32}$ is H or methyl; $R^{24}$ and $R^{25}$ are H.

3. An aqueous emulsion where the discontinuous phase comprises water and the continuous phase comprises the composition of claim 1.

4. An aqueous emulsion where the discontinuous phase comprises water and the continuous phase comprises the composition of claim 2.

5. An aqueous emulsion where the discontinuous phase comprises the composition of claim 1 and the continuous phase comprises water.

6. An aqueous emulsion where the discontinuous phase comprises the composition of claim 2 and the continuous phase comprises water.

7. A non-aqueous emulsion where the discontinuous phase comprises a non-aqueous hydroxylic solvent and the continuous phase comprises the composition of claim 1.

8. A non-aqueous emulsion where the discontinuous phase comprises a non-aqueous hydroxylic solvent and the continuous phase comprises the composition of claim 2.

9. A non-aqueous emulsion where the continuous phase comprises a non-aqueous hydroxylic organic solvent and the discontinuous phase comprises the composition of claim 1.

10. A non-aqueous emulsion where the continuous phase comprises a non-aqueous hydroxylic organic solvent and the discontinuous phase comprises the composition of claim 2.

\* \* \* \* \*